(12) United States Patent
Beran

(10) Patent No.: US 10,729,888 B2
(45) Date of Patent: Aug. 4, 2020

(54) SECUREMENT DEVICE FOR IV CATHETERS

(71) Applicant: Anthony V Beran, Yorba Linda, CA (US)

(72) Inventor: Anthony V Beran, Yorba Linda, CA (US)

(*) Notice: Subject to any disclaimer, the term of this patent is extended or adjusted under 35 U.S.C. 154(b) by 322 days.

(21) Appl. No.: 15/330,188

(22) Filed: Aug. 19, 2016

(65) Prior Publication Data

US 2016/0367789 A1 Dec. 22, 2016

Related U.S. Application Data

(63) Continuation-in-part of application No. 13/986,351, filed on Apr. 23, 2013, now Pat. No. 9,526,869.

(51) Int. Cl.
*A61M 25/02* (2006.01)

(52) U.S. Cl.
CPC ....... *A61M 25/02* (2013.01); *A61M 2025/024* (2013.01); *A61M 2025/026* (2013.01); *A61M 2025/0266* (2013.01)

(58) Field of Classification Search
CPC .......... A61M 2025/0266; A61M 25/02; A61M 2025/0246; A61M 2025/0273
See application file for complete search history.

(56) References Cited

U.S. PATENT DOCUMENTS

| 7,354,421 B2* | 4/2008 | Bierman | A61M 25/02 604/174 |
| 2015/0224285 A1* | 8/2015 | Howell | A61M 25/02 604/180 |

* cited by examiner

*Primary Examiner* — Deanna K Hall
(74) *Attorney, Agent, or Firm* — Gordon E. Gray, III; Gray Law Firm

(57) ABSTRACT

The present invention pertains to a device for securing a medical implement to the body of a patient such as an IV catheter. The device preferably comprises a base with an insertion site viewing window connected to a luer interconnection cushion at an articulation point and separated from the cushion by a gap. The bottom surface has an adhesive. The device further has a cover with a luer interconnection window, where the bottom surface of the cover also has an adhesive to secure a luer lock of a catheter. The device can also be placed on the Luer interconnection cushion to secure a central IV catheter. The device preferably is made of adhesive foam padding and the insertion site window is polyurethane film. The cover can be connected to the cushion at a lateral pivot. The device can be stored on release paper until used.

5 Claims, 25 Drawing Sheets

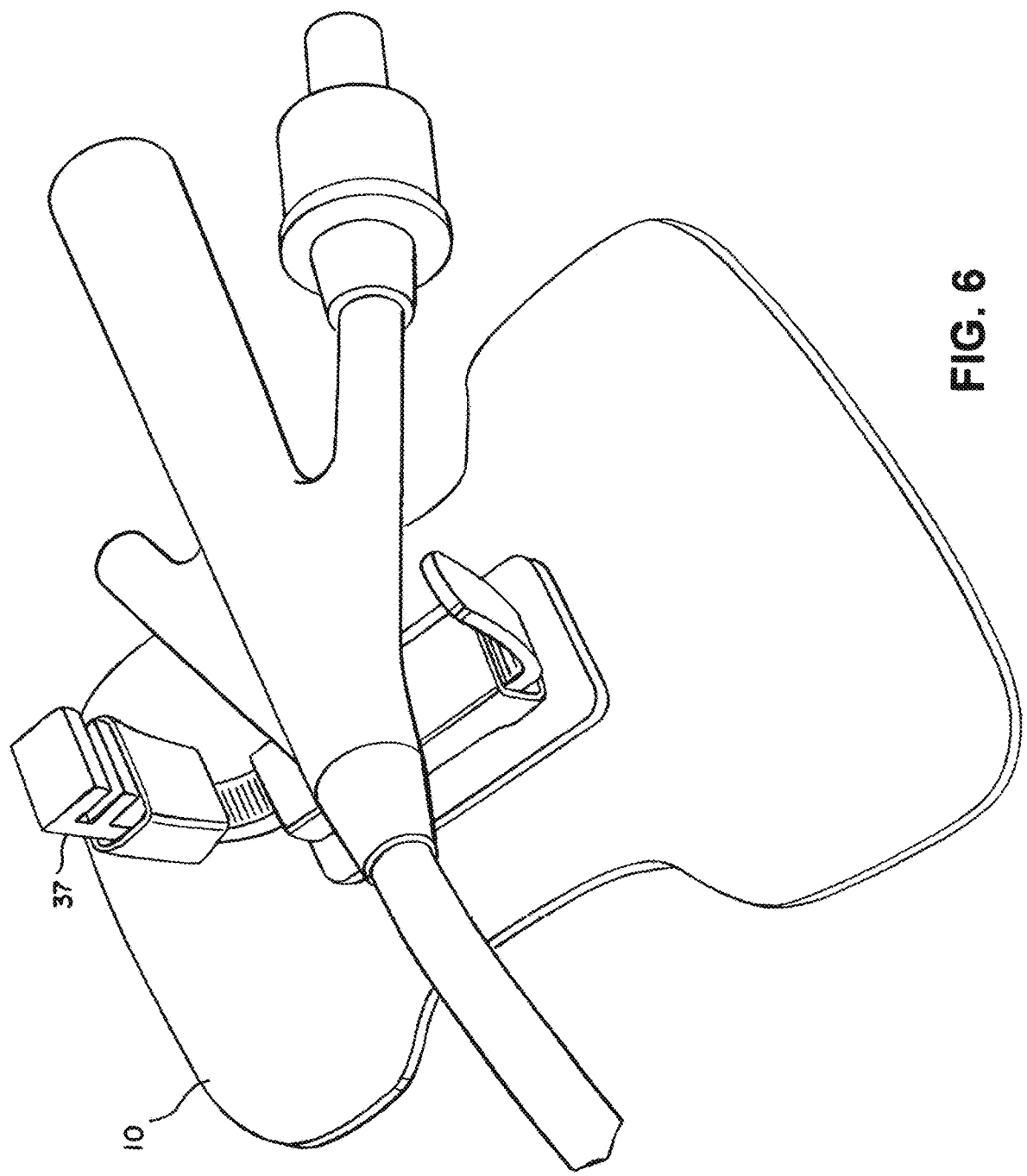

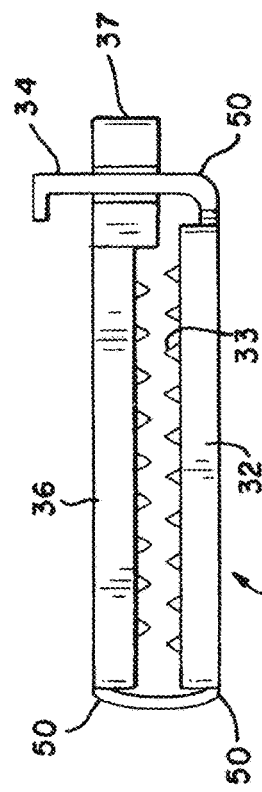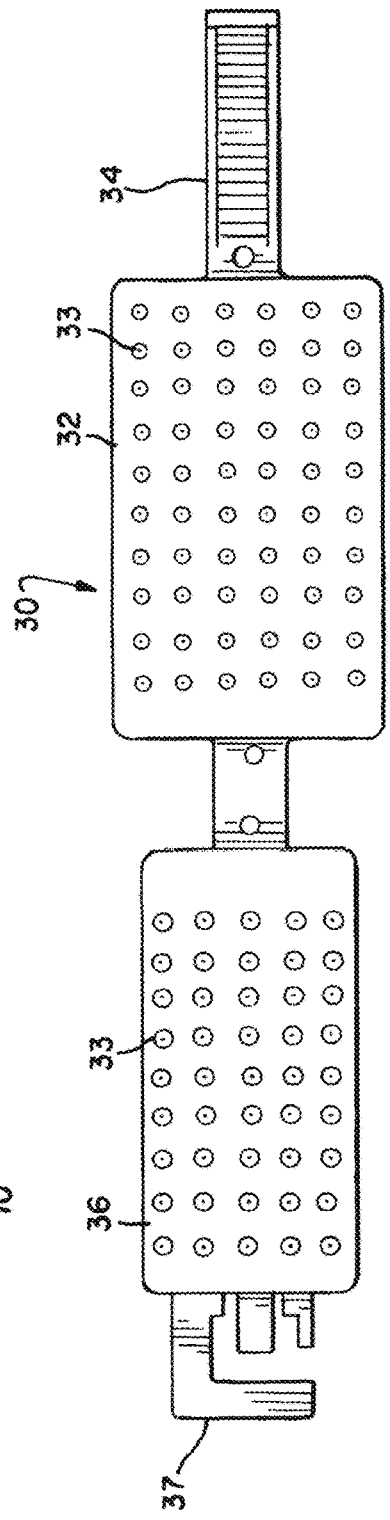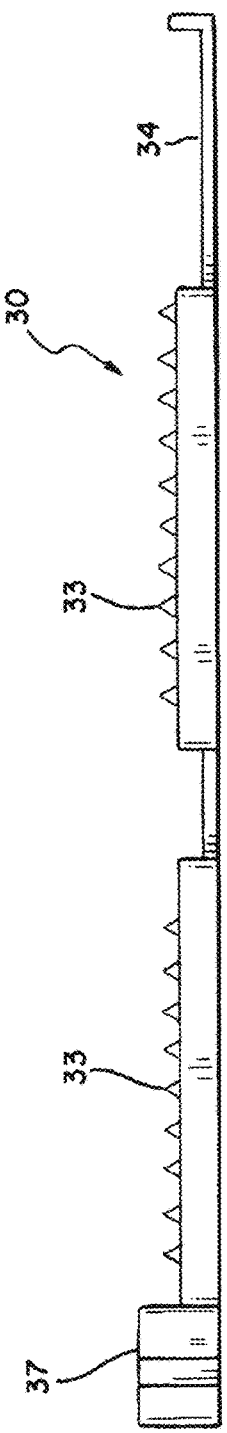

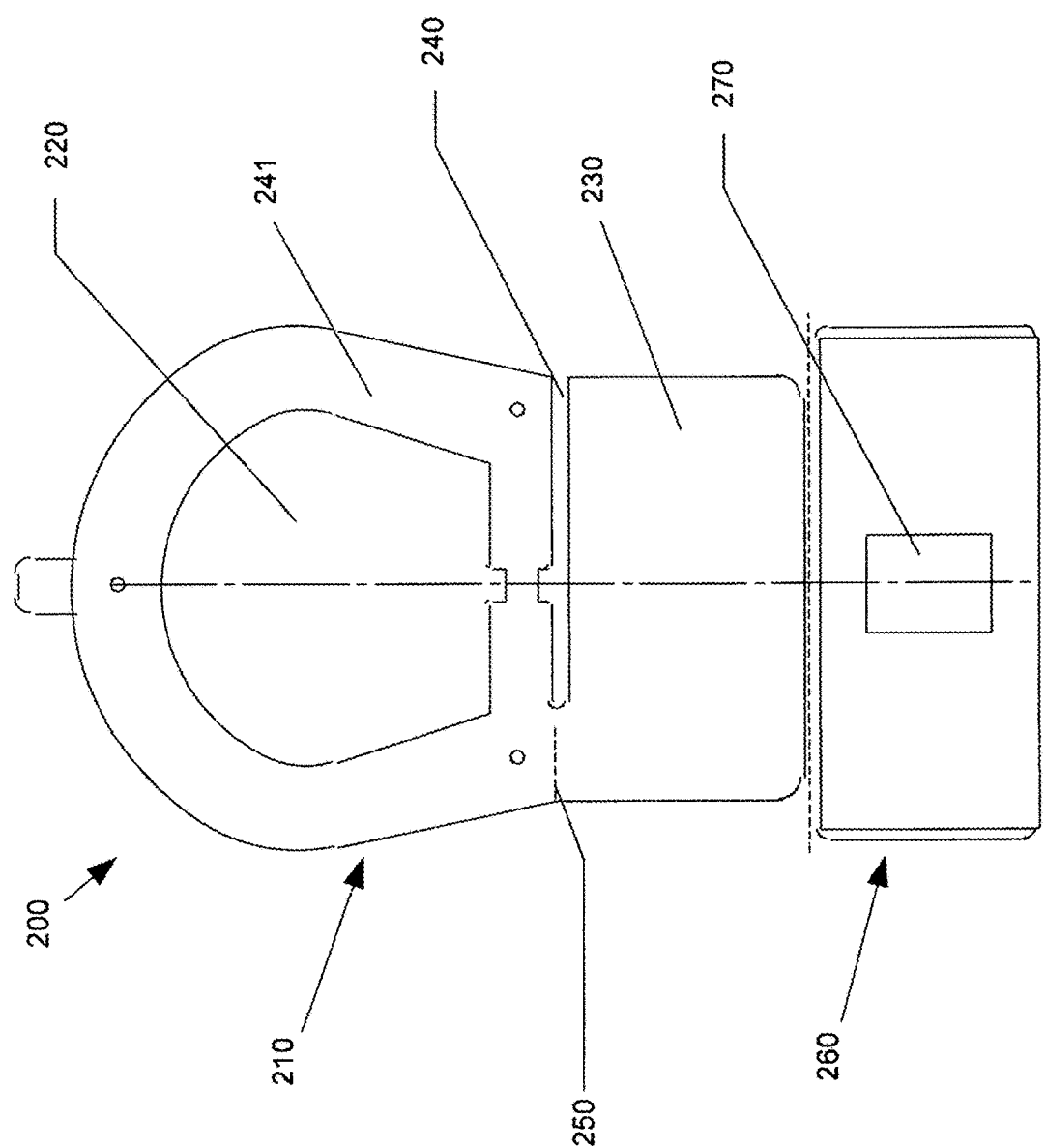

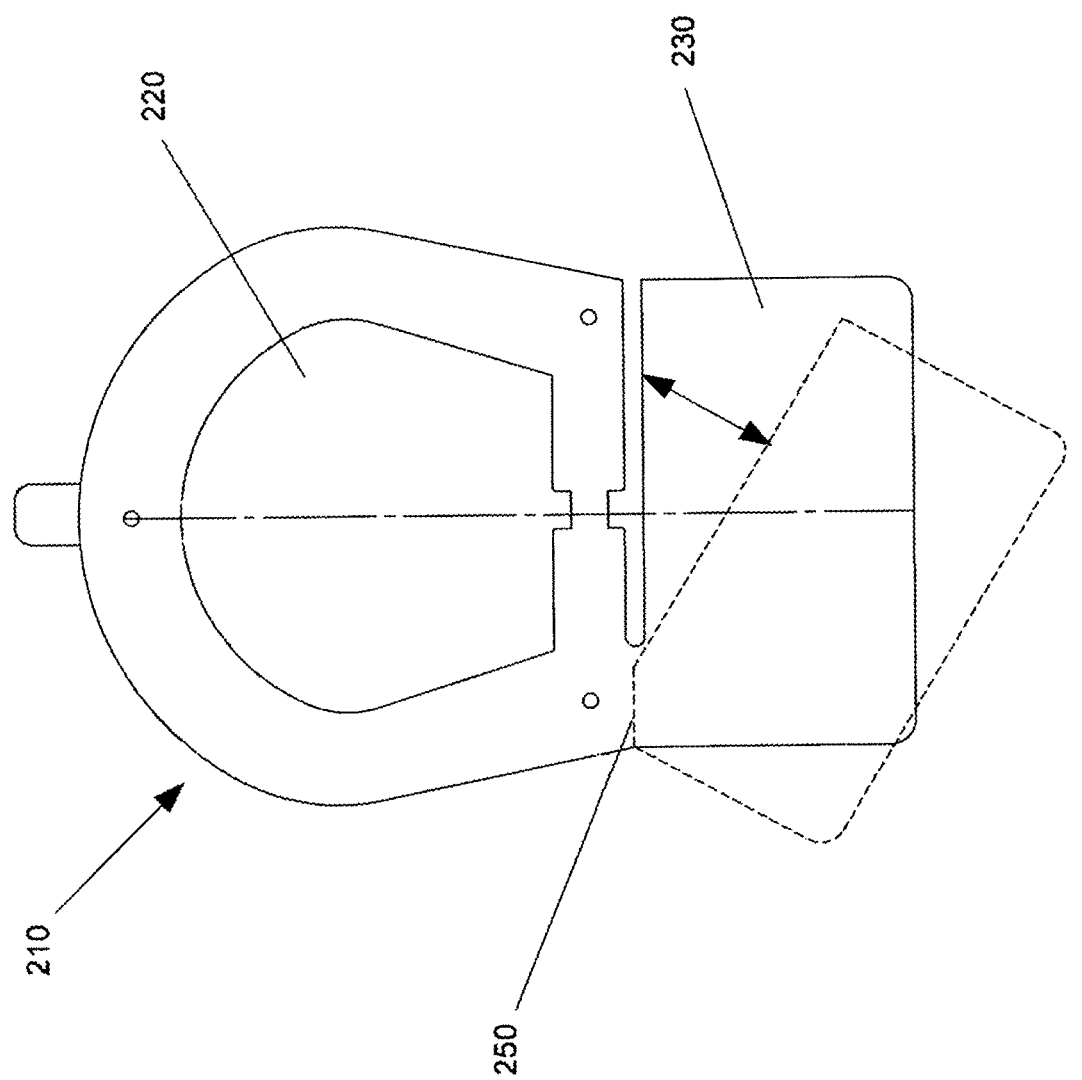

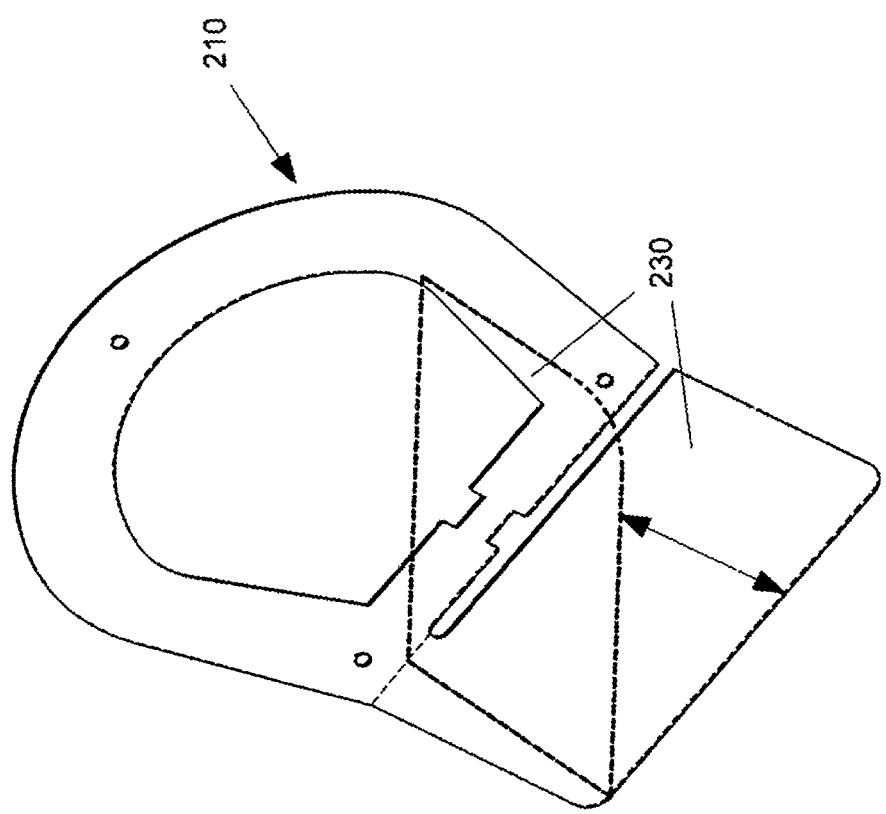

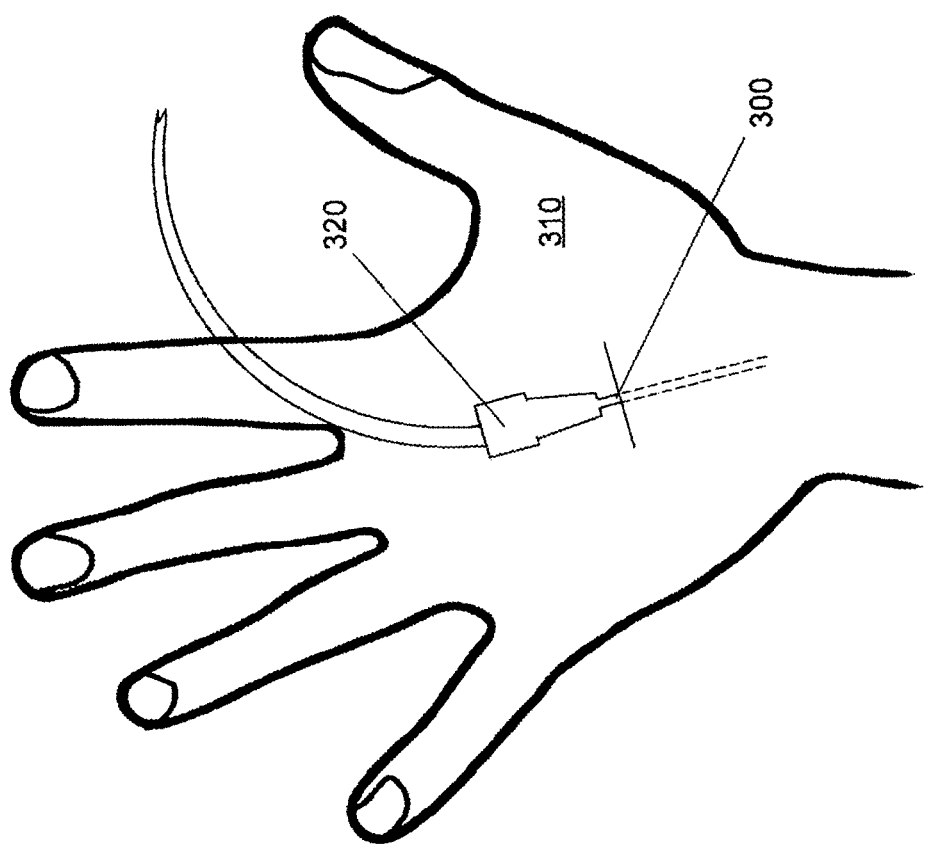

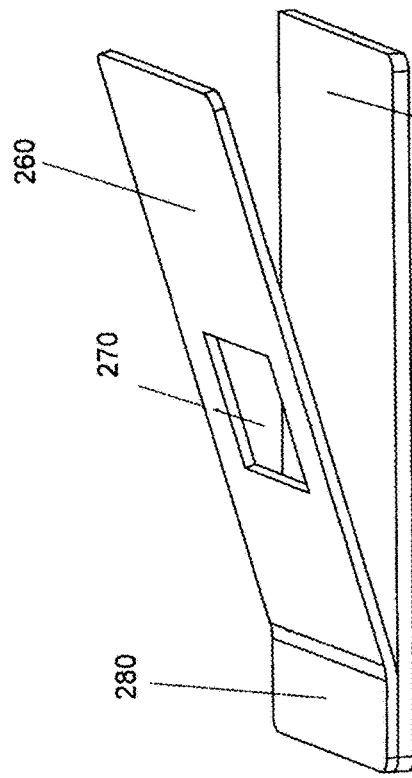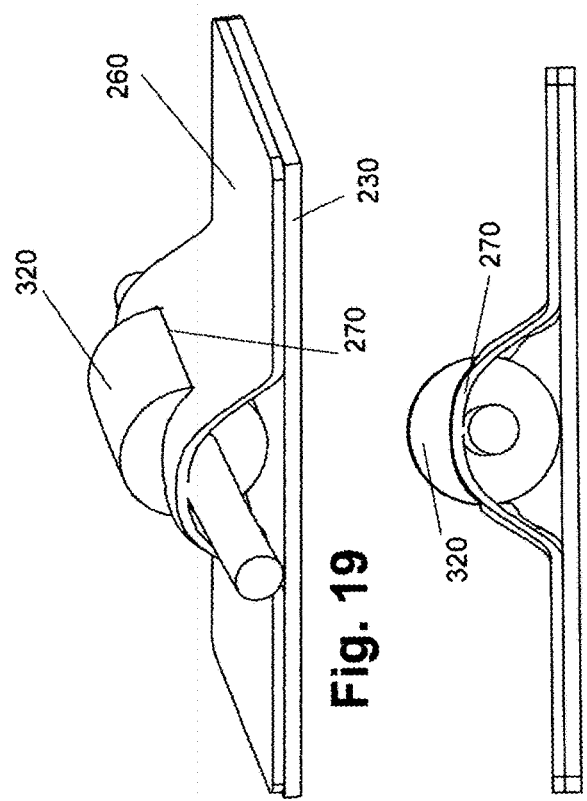

SECUREMENT DEVICE FOR IV CATHETERS

This is a continuation-in-part application of Ser. No. 13/986,351, filed Apr. 23, 2013. Said patent application is incorporated herein by reference in its entirety.

TECHNICAL FIELD

The present invention pertains to a device for securing a medical implement to the body of a patient such as an IV catheter.

BACKGROUND ART

Medical implements such as catheters, tubes and lines often must be used on patients and left in place. Accordingly, these items can be attached to a patient by various devices such as those disclosed in U.S. Pat. Nos. 7,922,697 and 4,392,857. Other prior art patents include: U.S. Pat. Nos. 3,900,026; 3,645,835; 5,116,324; 5,372,589; 5,885,254; 6,841,715; 7,294,752; and 8,881,899 and U.S. Design Pat. No. 252,822. Other prior art patent publications include: US2002/0188255 and US2006/02648836.

However, these devices can be either overly complex, bulky or not compatible with various medical implements. Thus, a simpler and more versatile securement device that would provide better securement with minimal movement and micro-pistoning when in situ is desired.

SUMMARY OF THE INVENTION

The present invention pertains to a device for securing a medical implement to the body of a patient such as an IV catheter. The device preferably comprises a base with an insertion site viewing window connected to a luer interconnection cushion at an articulation point and separated from the cushion by a gap. The bottom surface has an adhesive. The device further has a cover with a luer interconnection window, where the bottom surface of the cover also has an adhesive to secure a luer lock of a catheter. The device can also be placed on the Luer interconnection cushion to secure a central IV catheter. The device preferably is made of adhesive foam padding and the insertion site window is polyurethane film. The cover can be connected to the cushion at a lateral pivot. The device can be stored on release paper until used.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 6 is a top perspective view of a preferred embodiment of the invention in an open position with a catheter in place;

FIG. 7 is a side view of an alternative embodiment of the invention without pads in a closed position;

FIG. 8 is a top view of an alternative embodiment of the invention without pads in an open position;

FIG. 9 is a side view of an alternative embodiment of the invention without pads in an open position;

FIG. 10 is top view of a preferred embodiment of the securement device for peripheral IV catheters;

FIG. 11 is a top view of the preferred embodiment in FIG. 10 showing longitudinal and transverse articulation of the luer interconnection cushion at the articulation point located between Luer interconnection cushion and a base;

FIG. 12 is a perspective top view of the preferred embodiment in FIG. 10 showing transverse articulation of the luer interconnection cushion at the articulation point between the cushion and the base;

FIG. 13 is a top view of a peripheral IV catheter insertion in a patient;

FIG. 18 is side perspective view of the luer interconnection securement device without the insertion site protection and viewing window;

FIG. 19 is a side perspective view of the luer interconnection securement device holding the luer interconnection and without the insertion site protection and viewing window where the Luer lock hub is protruding through the window;

FIG. 20 is side view of the luer interconnection securement device holding the luer interconnection and without the insertion site protection and viewing window;

DETAILED DESCRIPTION OF THE PREFERRED EMBODIMENTS

Figure 1:
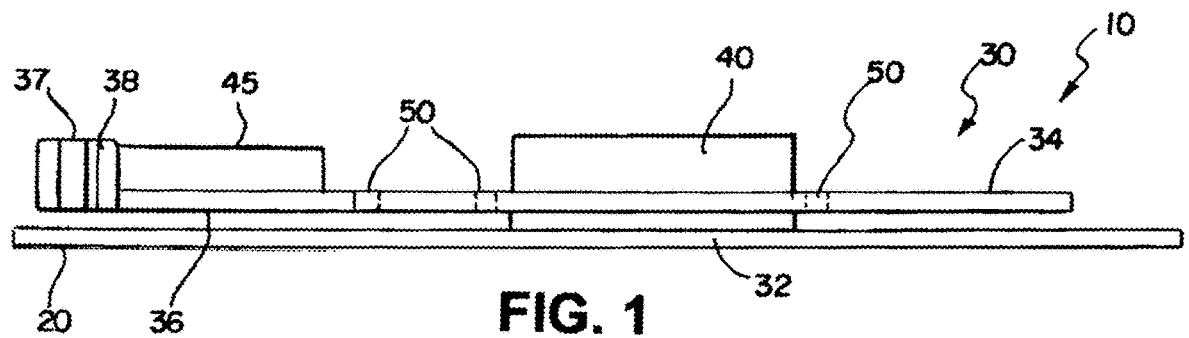
FIG. 1 is a side view of a preferred embodiment of the invention in an open position.

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident, however, that such embodiment(s) may be practiced without these specific details.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s). The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved securement device for peripheral and central IV catheters.

Referring now to FIG. 1, a side view of a preferred embodiment of the invention 10 is shown in an open position. The preferred embodiment shown in FIG. 1 has a base pad 20 with a top and bottom surface, where at least a portion of the bottom surface of the pad 20 has an adhesive. The adhesive is preferably suitable for attaching the device to the body of a patient and can be any hypoallergenic adhesive suitable for skin application.

Figure 3:
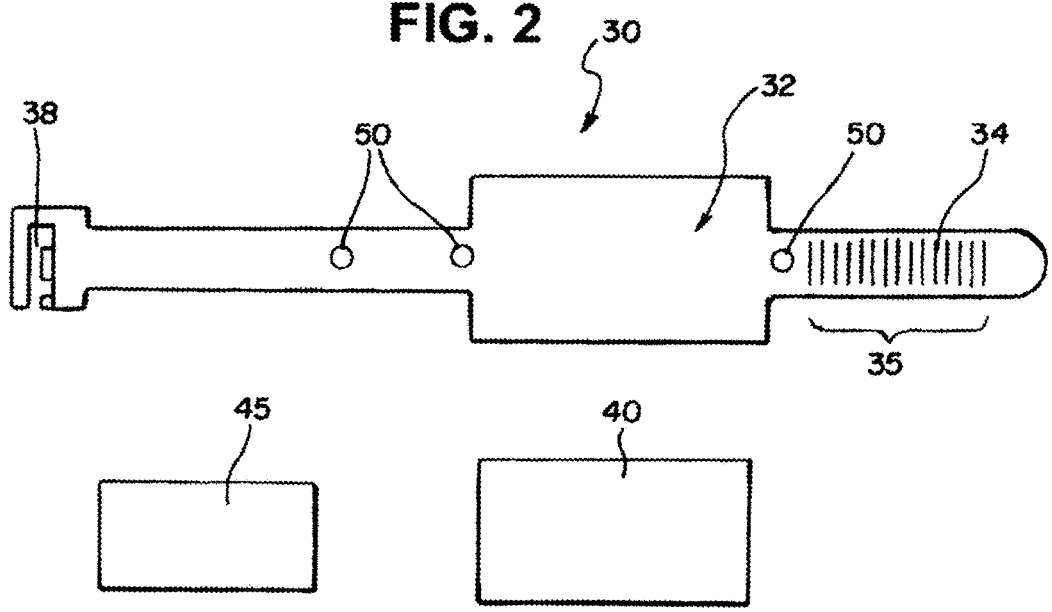
FIG. 3 is a top partially exploded view of a preferred embodiment of the securement member.

A securement member 30 is preferably attached to the top surface of the base pad 20. The securement member 30 shown in FIG. 1 has a member base 32 with a gear rack 34 extending from a first side and a locking device 36 extending from a second side. The gear rack 34 shown in FIG. 1 is connected to the member base 32 by a living hinge 50. The locking device 36 shown in FIG. 1 is connected to the member base by a set of living hinges 50. The gear rack 34 preferably has notches 35 as shown in FIG. 3. The notches 35 are preferably used to interact with the locking device 36. The locking device 36 shown has a lock case 37 with an open side and a ratchet 38, where the ratchet 38 engages with the notches 35. The locking device 36 can be disengaged by removing the ratchet 38 from the notches 35, e.g. using the open side of the lock case 37.

A center pad 40 is preferably mounted on the member base 32. The center pad 40 is preferably a foam pad with a plastisol sleeve or plastisol film coating, or a non-skid pliable plastic material. A lock pad 45 is preferably mounted on the locking device 36 next to the lock 37. The lock pad 45 is preferably a foam pad with a plastisol sleeve or plastisol film coating, or a non-skid pliable plastic material. The securement member 30 is preferably a single integrated unit created by injection molding of plastic such as nylon. The member base 32 is preferably rigid and the locking device 36 and gear rack 34 are preferably flexible.

Figure 2:
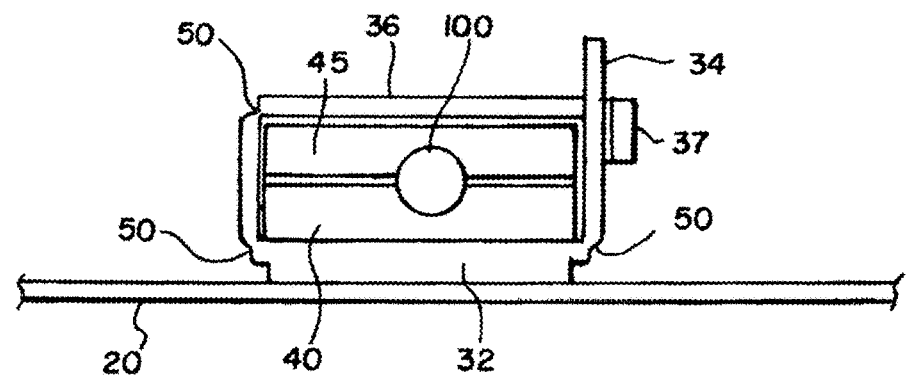
FIG. 2 is a side view of a preferred embodiment of the invention in a closed position.

Referring now to FIG. 2, a side view of the preferred embodiment shown in FIG. 1 is shown in the closed position. As shown, the gear rack 34 is insert into the side opening of the lock case 37 on the locking device 36. The gear rack 34 is preferably held in the lock case 37 by the engagement of the ratchet 38 on the notches 35 of the gear rack 34. The securement member 30 can be adjusted for a looser or tighter fit around a medical implement, e.g. a catheter 100, using the gear rack 34 and lock case 37 with ratchet 38. Preferably, the pads 40 and 45 are deformable around the implement 100 for a tighter hold on the implement 100. The living hinges 50 preferably bend to allow the securement member 30 to move between the open position in FIG. 1 and the closed position in FIG. 2, and depending on the location and number of living hinges 50, the hinges 50 allow the securement member 30 to form a desired geometry to secure objects of different geometry and size. The living hinges 50 allow the invention to close into a more compact form, namely the closed position, while keeping the device simple in operation.

Figure 4:
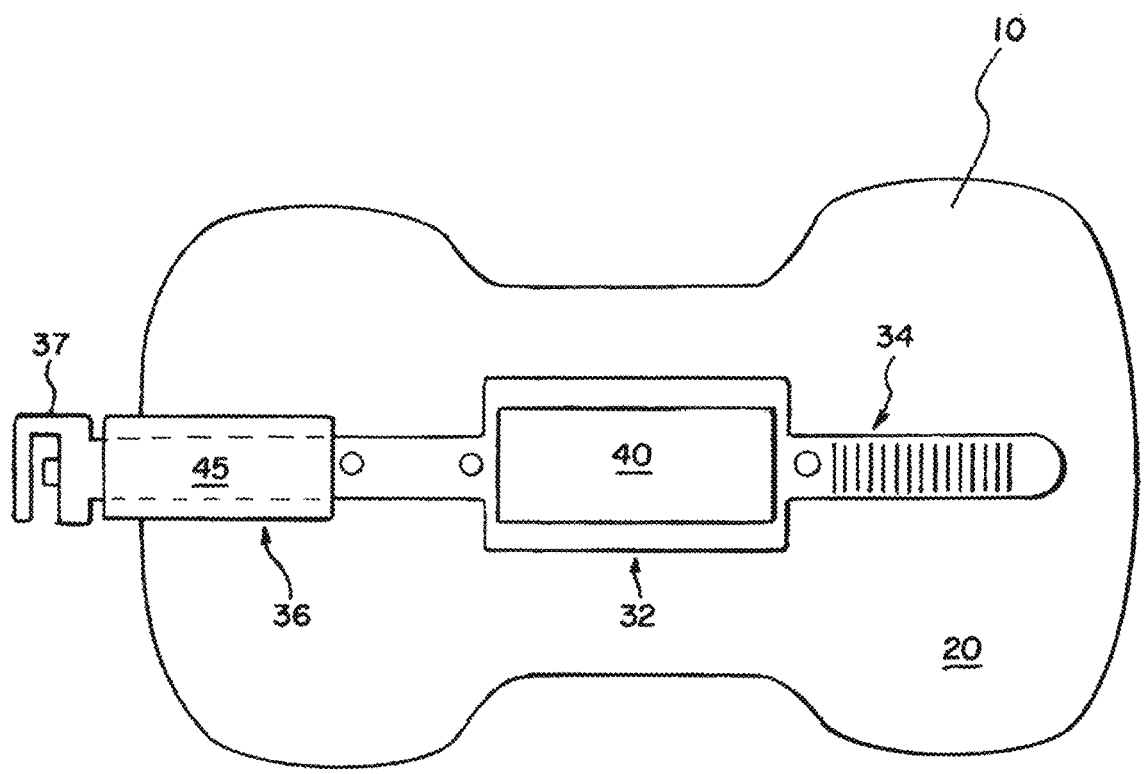
FIG. 4 is a top view of a preferred embodiment of the invention in an open position.

Referring now to FIG. 4, a top view of a preferred embodiment of the invention 10 is shown in an open position. The preferred embodiment shown in FIG. 4 is preferably for use to secure a central venous catheter and/or other catheters or tubes. FIG. 6 shows a preferred embodiment in an open position with a catheter in place.

Figure 5:
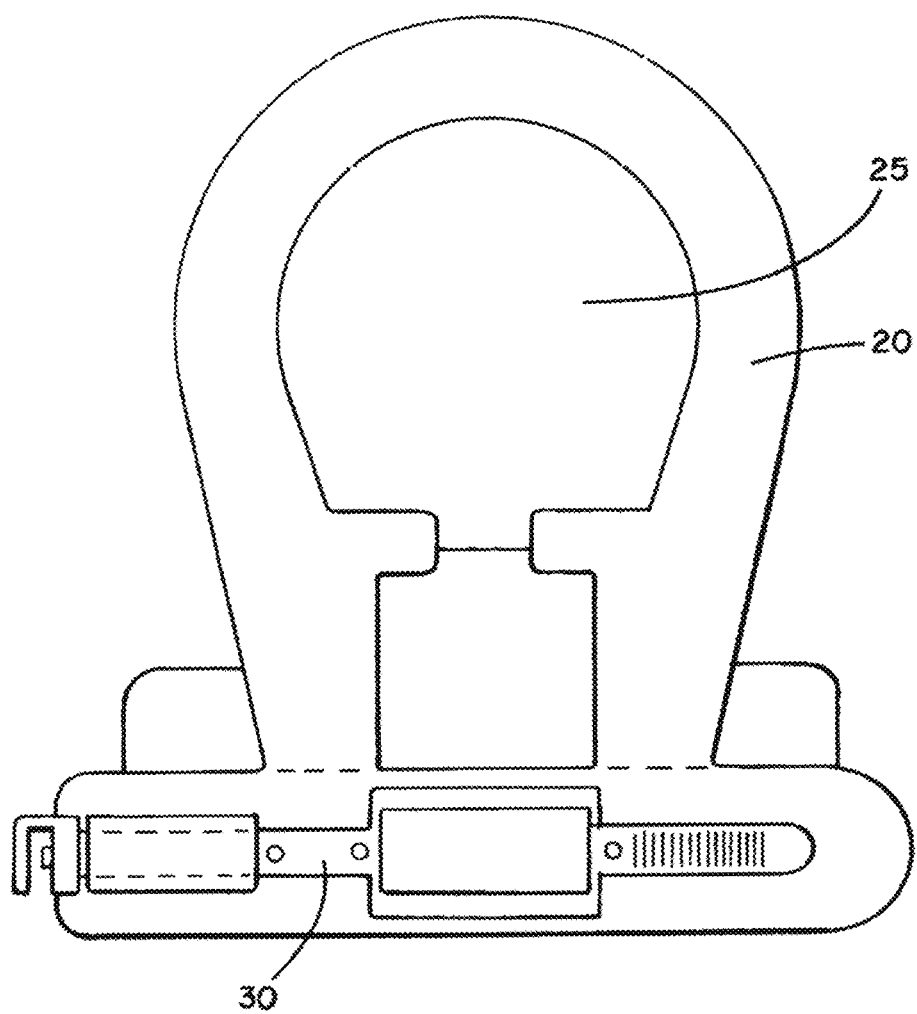
FIG. 5 is a top view of an alternative embodiment of the invention where the base pad further comprises a transparent window.

Referring now to FIG. 5, a top view of another preferred embodiment of the invention 10 is shown in an open position. In FIG. 5, the alternative embodiment is preferably used for securement of peripheral intravenous ("IV") catheters and/or line. The base pad 20 still preferably uses an adhesive on its bottom side for attachment to a patient. However, the base pad 20 further comprises a transparent window 25 with hypoallergenic adhesive, where the window 25 is usually made of clear urethane co-polyester film. The securement member 30 is then preferably mounted at the perimeter of the pad 20.

Referring now to FIG. 7, another alternative embodiment of the securement member 30 is shown in a closed position. This alternative embodiment preferably does not use pads as described above. Instead, the member base 32 and locking device 36 have teeth 33 protruding from interior surfaces, namely the base securement and lock securement surfaces.

The alternative embodiment is shown in open position in FIGS. 8 and 9. The teeth 33 or other protrusions such as bumps preferably are used to grip items in the device such as medical implements, pads or bandages. Again, the alternative embodiment shown in FIGS. 7-9 preferably has living hinges 50 that allow the securement member 30 to be more compactly closed into different sizes and geometries.

Alternative Embodiment for Securement Device for IV Catheters

Referring back to FIG. 5, an alternative embodiment for a securement device for IV catheters is shown and described. Referring now to FIG. 10, another alternative embodiment of a securement device for IV catheters is shown. The invention 200 has a base 210, preferably comprising an insertion site window 220 bordering with foam structure 241 and separated from a luer interconnection cushion 230 by a partial gap 240 and connected to the luer interconnection cushion 230 by an articulation point 250. The invention 200 further comprises a cover 260 having a luer interconnection window 270. Preferably, the base 210 and cover 260 comprise adhesive foam padding such as DE foam with acrylic adhesive or other hypoallergenic adhesives. Preferably, the window 220 preferably comprises polyurethane film (or other film). Additionally, the base 210 has a top surface and a bottom surface where the bottom surface preferably has adhesive so the base can be affixed to patients. The cover 260 also preferably has adhesive so it can be adhered to the luer interconnection cushion 230 with the Luer lock connection protruding through the window to hold a peripheral IV catheter in place on a patient.

Figure 14:
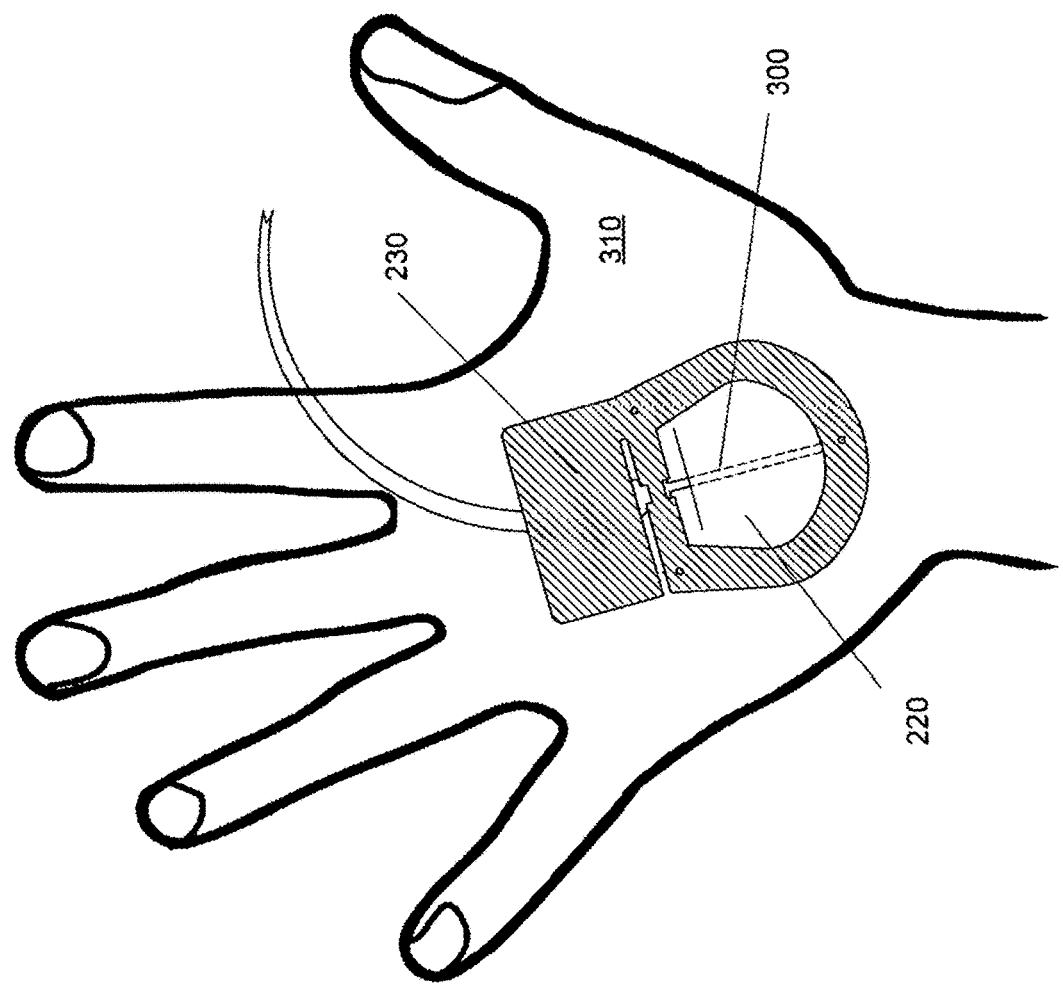
FIG. 14 is a top view of the preferred embodiment in FIG. 10 with an initial placement over a peripheral IV catheter insertion the cushion is over the Luer Lock and connecting line.
Figure 15:
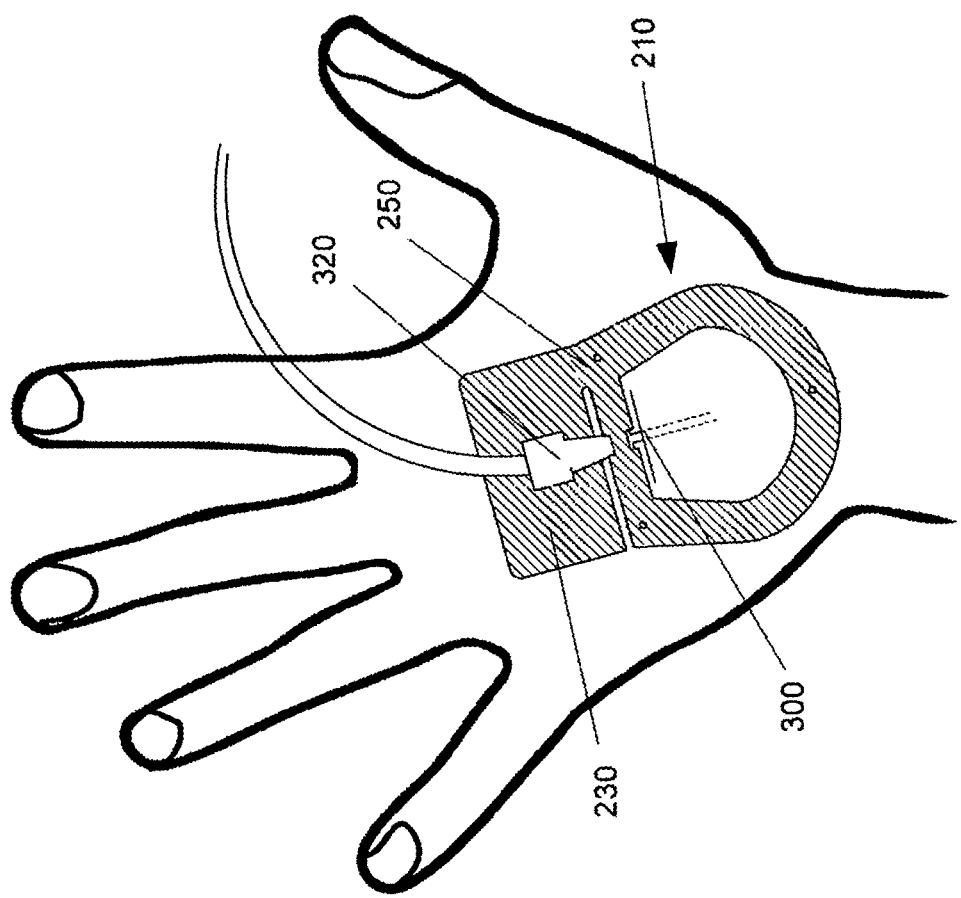
FIG. 15 is top view of the preferred embodiment in FIG. 10 after the luer interconnection cushion by transverse and longitudinal movement at the articulation point, is moved under the luer lock interconnection and secured to the skin of the patient.

Referring now to FIG. 11, the luer interconnection cushion 230 for the embodiment shown in FIG. 10 is shown with longitudinal and transverse articulation in relationship to the base 210, which is attached to the patient. The articulation point 250 facilitates the longitudinal and transverse articulation, which permits cushion 230 to be moved from above the medical implement to below the medical implement when base 210 is already fixed to the patient. Referring now to FIG. 12, the luer interconnection cushion 230 for the embodiment shown in FIG. 10 is shown with transverse articulation. This bi-direction articulation more easily allows the base 210 to be place over a typical catheter insertion point 300 as shown in FIGS. 13 and 14. The insertion site window 220 is placed over the catheter insertion site 300 and adhered to the skin 310 of the patient. As shown in FIG. 14, the luer interconnection cushion 230 lays over the luer lock 320. However, by longitudinal and transverse movement of the luer interconnection cushion 230 at the articulation point 250, the cushion 230 is placed under the luer lock 320 and secured to the skin of the patient 310 with the adhesive on the bottom layer as shown in FIG. 15.

Figure 16:
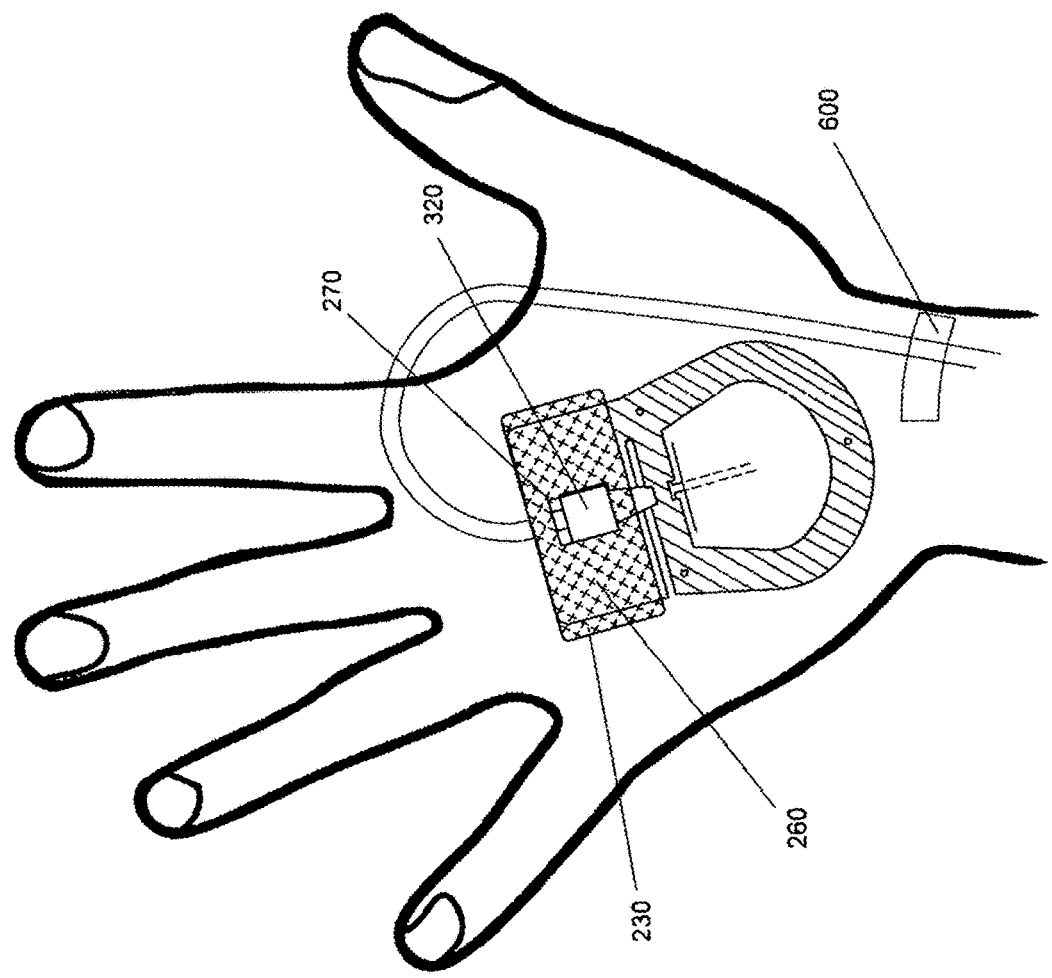
FIG. 16 is a top view of the preferred embodiment in FIG. 10 where the cover is placed over the luer interconnect and attached to the luer interconnection cushion.

Referring now to FIG. 16, the cover 260 is placed over the catheter hub and connecting line with Luer lock 320 protruding through the interconnection window 270 and is attached to the cushion 230 with adhesive. The luer lock 320 is preferably visible through the luer interconnection window 270. By allowing the Luer lock hub to pass through the window 270, less pressure is transferred to the skin and better securement is accomplished.

Figure 17:
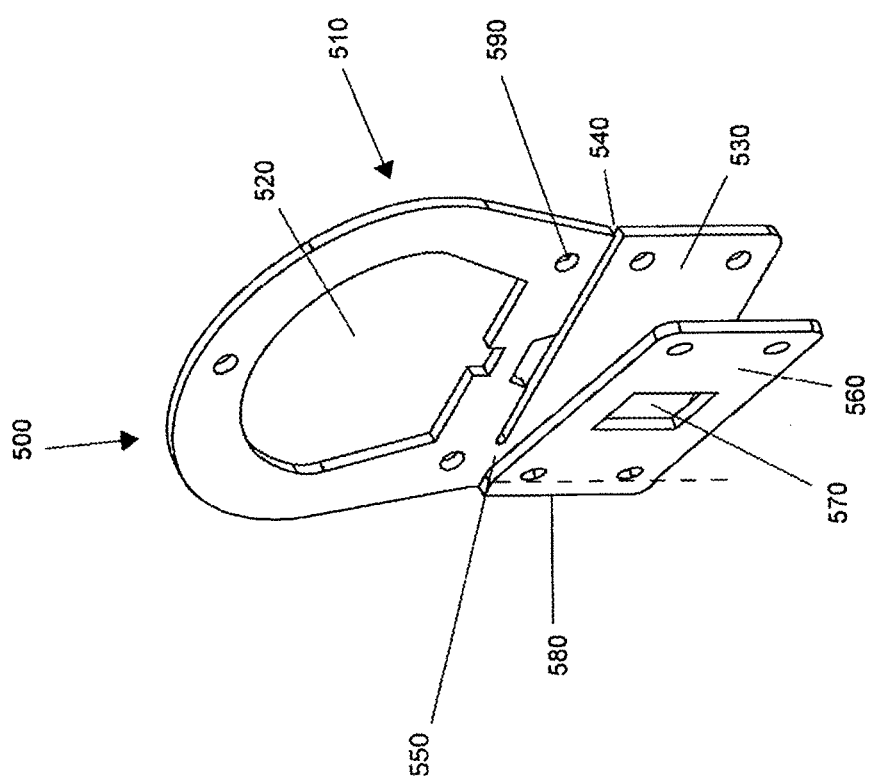
FIG. 17 is top perspective view of an alternative embodiment of a securement device for peripheral IV catheters where the cover is attached to the base along the lateral pivot.

Referring now to FIG. 17, yet another alternative embodiment is shown. This embodiment 500 has a base 510, preferably comprising an insertion site window 520 separated from a luer interconnection cushion 530 by a partial gap 540 and connected to the luer interconnection cushion 530 by an articulation point 550. The embodiment 500 further comprises a cover 560 having a luer interconnection window 570. The cover 560 is attached to the cushion 530 at a lateral pivot 580.

Additionally, the base 510 has a top surface and a bottom surface where the bottom surface preferably has adhesive so the base can be affixed to patients. The cover 560 also preferably has adhesive so it can be adhered to the cushion 530 to hold a peripheral IV catheter or a central IV catheter in place on a patient. Velcro® also could be used instead of adhesive to secure a medical device between the cover 560 and the cushion 530. The base 510 and cushion 530 also preferably have a number of breather holes 590.

The articulation point 550 and the lateral pivot 580 provide multiple axes of articulation for the device 500 including longitudinal and traverse. Transverse articulation between the luer connection cushion 530 and the cover 560 occurs along the lateral pivot 580.

Preferably, an independent anchoring strip 600 is used to secure any catheter or infusion needle associated tubing upstream of the insertion site. The independent anchoring strip is shown in FIG. 16.

Referring now to FIG. 18, another alternative embodiment is shown where the securement structure no longer has the insertion site window 220, and, the cover 260 is attached to the cushion 230 at a lateral pivot 280. FIGS. 19 and 20 show the embodiment of FIG. 18 securing a luer lock 320 visible through the window 270.

Figure 21:
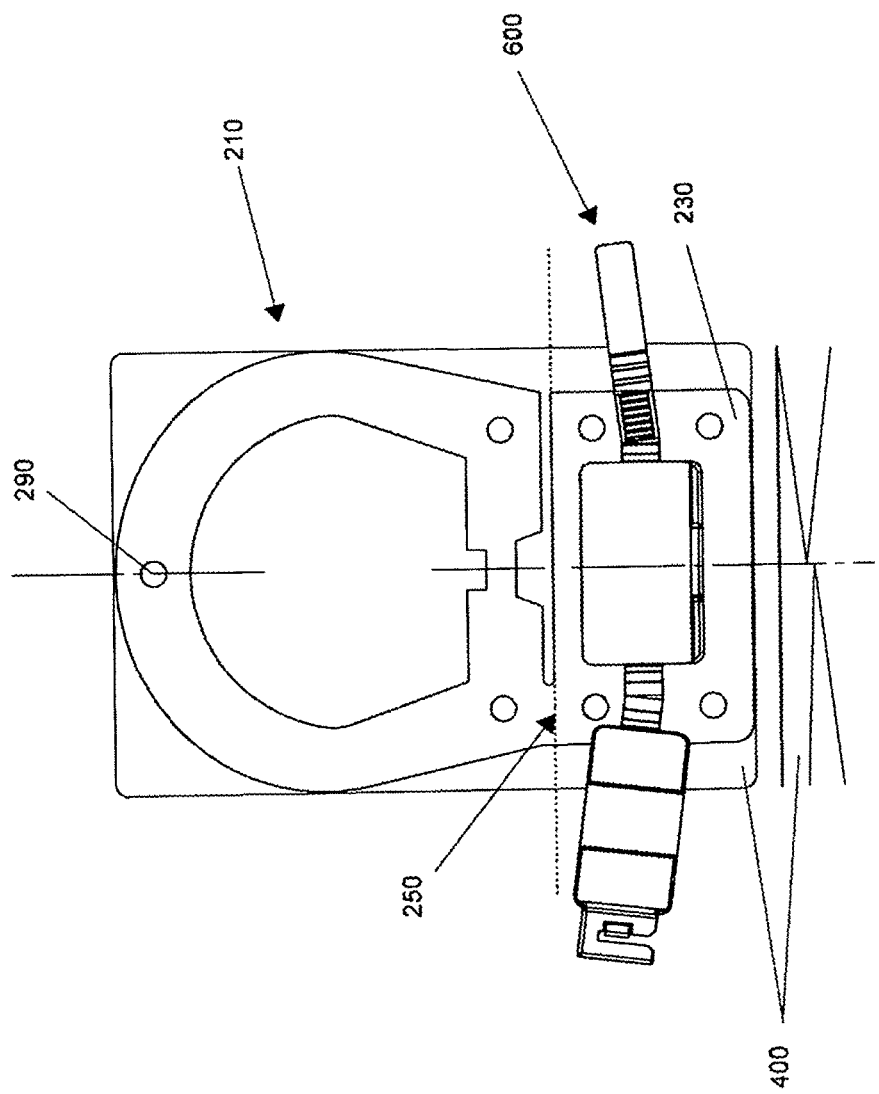
FIG. 21 is a top view of the catheter securement device shown in FIG. 5 combined with the embodiment of a securement device for peripheral IV catheters shown in FIG. 10 to provide a central IV catheter securement device with insertion site protection and viewing window.

Referring now to FIG. 21, another alternative embodiment is shown. This embodiment preferably comprises the embodiment of the FIG. 5 catheter securement device described above along with the embodiment shown in FIG. 10 for the securement device for a central IV catheter. The securement member 600 is attached to the cushion 230 to provide a combination device comprising a securement and insertion window with bio-occlusive dressing. FIG. 21 further shows the articulation point 250 that also comprises a set of perforations that allow for cushion 230 to separate from the base 210. This facilitates securement of the catheter at any distance from the base 210. Also shown in FIG. 21 is overlapping folded release paper 400 that preferably covers the bottom layer of the Luer interconnection cushion 230 to cover the adhesive and preserve the adhesive until the device 200 can be applied to a patient's skin and to provide for easy placement of insertion site window, over the catheter in situ, without the cushion sticking to the patient's skin. Also shown are breather holes 290 for the base 210 to provide improved airflow to the patient's skin while the device 200 is in place.

Figure 22:
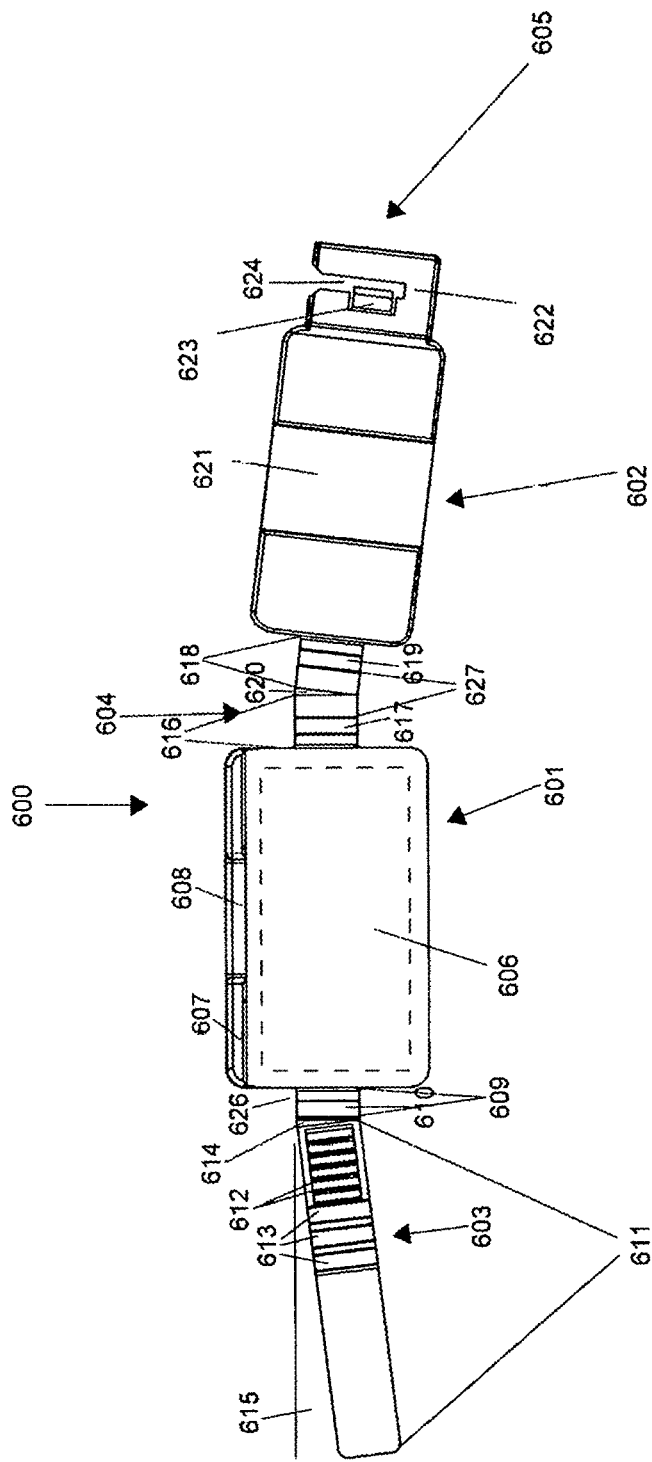
FIG. 22 is a top view of an alternate embodiment of a securement member for a central IV catheter.

Referring now to FIG. 22, a top view of a preferred embodiment of a securement member is shown. The securement member comprises a base 601 and a cover 602. The base 601 on one side extends to a gear rack strap 603 and, on the other side, is connected with the cover 602 by an articulation strap 604. The cover 602 terminates with a locking device 605. The base 601 has a top and a bottom surface. The bottom surface is attached to a Luer cushion 230 and the top surface accepts the catheter. The top surface has a non-skid structure and/or adhesive or adhesive film 606 placed over it. The base 601 also has a vertical ridge 607 which is positioned opposite to the open end and which has at least one cutout 608. The base 601 is also sloped from the ridge 607 toward an open end. The ridge 607 has a centrally located cut out 608. The gear rack strap 603 articulates with the base with one living hinge 610 that permits the gear rack strap 603 to move transversely from a horizontal to a vertical position in relationship to the base 601. The gear rack strap 603 has several horizontal notches and several living hinges above the notches. The gear rack strap 603 extends from the base 601 in two parts. The first part 609 houses the living hinge 610 and a second part 611 houses the notches 612 and the living hinges 613 on the opposite side. The two parts are separated by a "V" shaped space 614 extending the second part 611 at an angle 615 that is different from an angle 626 of the first part. The living hinge 610 of the first part 609 is preferably parallel with the base. The second part 611 is on an angle 615 in relationship to the base. The angle 615 is greater than 90 degrees, e.g. 90 to 130 degrees, and depends on the slope angle of the base 601. The angle 626 of the first part is preferably 90 degrees to the side of the base 601 but can be between 90 and 130 degrees.

Figure 24:
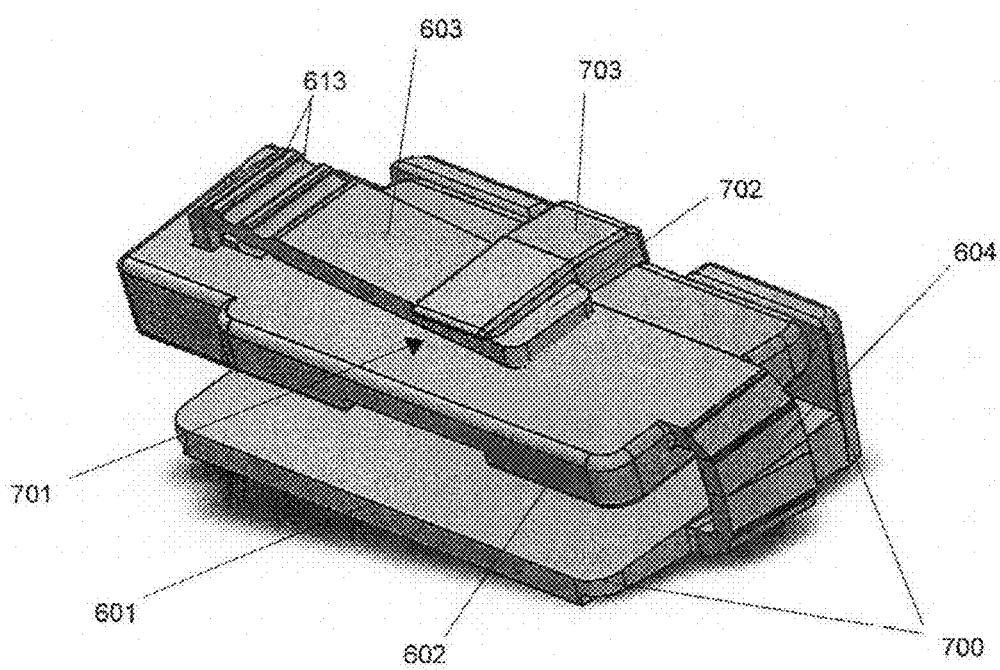
FIG. 24 is a perspective view of an alternative embodiment of a securement member for central IV catheter in a locked position.

The articulation strap 604 connecting the base 601 with the cover 602 comprises two parts. The first part 616 houses the living hinge 617 and the second part 618 houses another living hinge 619 which are separated from each other by a "V" shape space 620, extending the second part 618 on an angle in relationship to the base 601. These structures provide for living hinges 617, 619 to perform in a motion that brings the cover 602 in parallel to the sloped base 601. Because of the angular offset to the second part 618 (see FIG. 22), the structure provides for cover to articulate in a parallel plane with the sloped base 700, securing the medical implement as shown in FIG. 24. The articulation strap 604 also includes a solid transverse member 627 that is a solid structure between the two living hinges 617, 619. The articulation strap 604 provides for movement of the cover 602 from a horizontal to a vertical position utilizing living hinge 617 that is close to the base 601, and vertical to horizontal over the base position using the living hinge 619 close to the cover 602. The cover's bottom side may have at least one channel 621 to accommodate irregular catheter structure. The cover 602 terminates with the primary locking device 605. The locking device 605 comprises a locking case 622 and a ratchet with teeth 623. It has a side opening 624 to permit the sliding of the gear rack 611 into the locking case 622 and allows for engagement of gear rack notches 612 with the teeth of the ratchet 623.

A secondary locking site 701 is shown in FIG. 24. This locking site 701 comprises an angle 703 centrally located on the top surface of the cover 602. The short side of the angle 703 is vertically integrated with the cover, so that the long side of the angle 703 extends over the cover 602 creating a slot 702 between the top surface of the cover and the bottom surface of the angle 703. The securement member is locked in place by joint action of the first and second locking site 701. The first locking site, by interaction between gear rack notches 612 and ratchet teeth 623 locks and secures the medical implement between the base 601 and the cover 602. The secondary locking site 701 uses the set of living hinges 613 and permits the gear rack strap 603 to bend 90° and to be placed into the slot 702 of the secondary locking site, preventing the gear rack strap 603 from disengaging from the ratchet of the locking device 605 as shown in FIG. 24.

Figure 23:
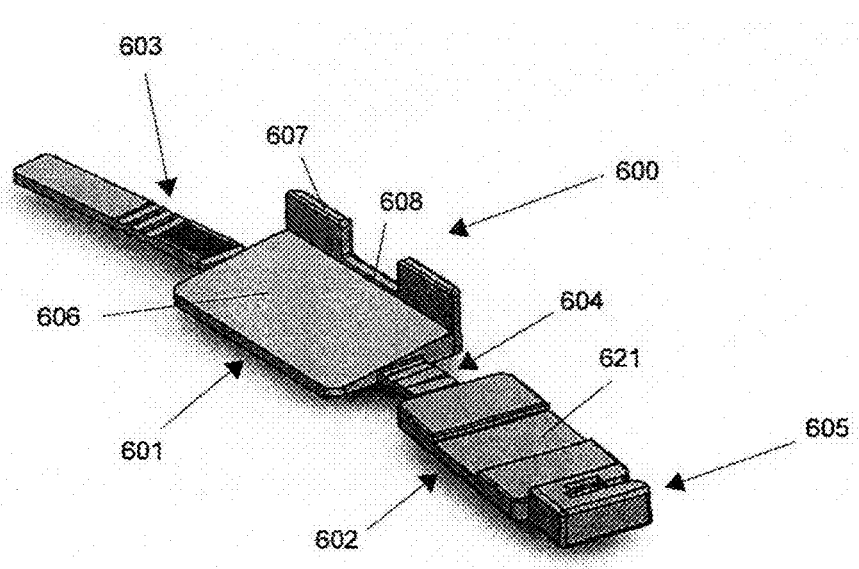
FIG. 23 is a perspective view of an alternative embodiment of a securement member for a central IV catheter.

Referring now to FIG. 23, a perspective view of a preferred embodiment of a securement member is shown. The surface 606 of the base 601 is sloped from the ridge 607 toward an open side. The gear rack strap 603 and articulation strap 604 are angled in relationship to the base 601. The ridge 607 has at least one cut out 608.

Figure 25:
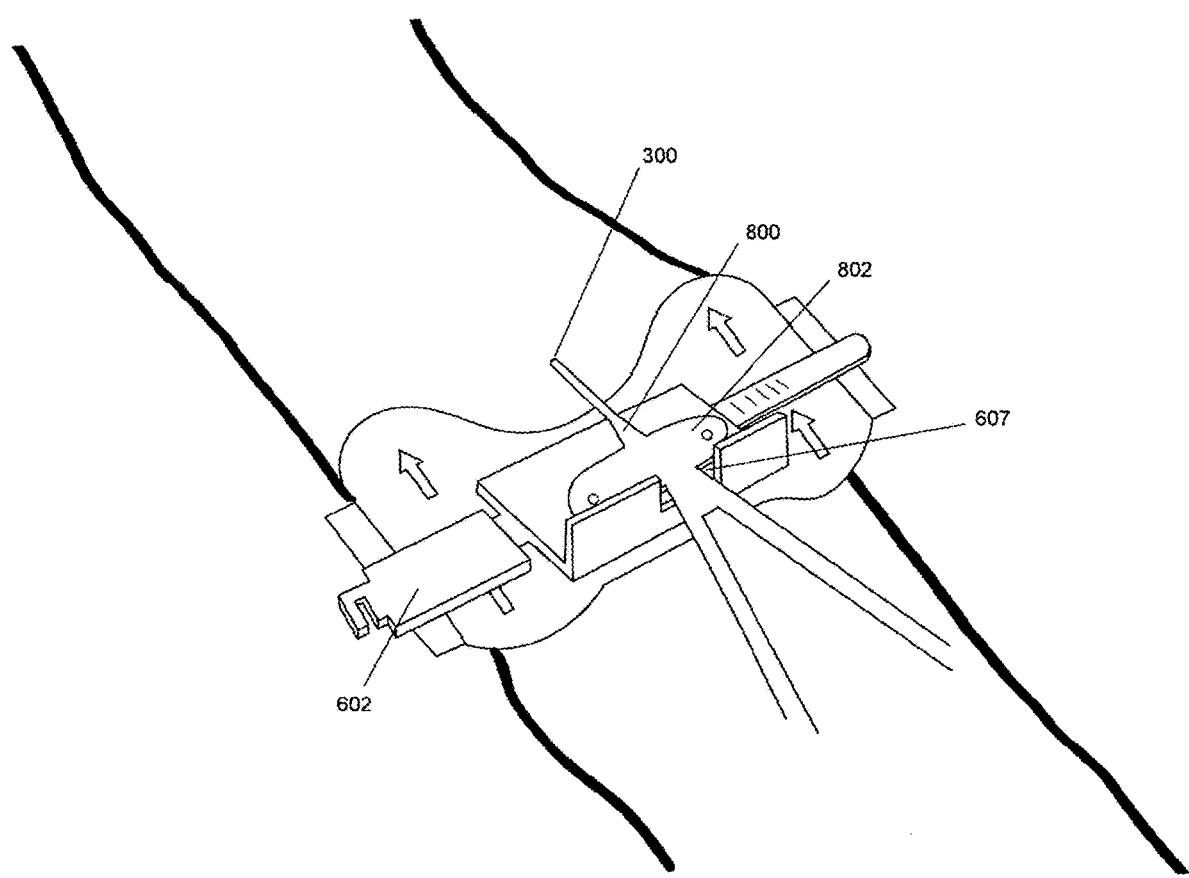
FIG. 25 is a top view of preferred embodiment with initial placement on the patient under a wing of the central IV catheter.
Figure 26:
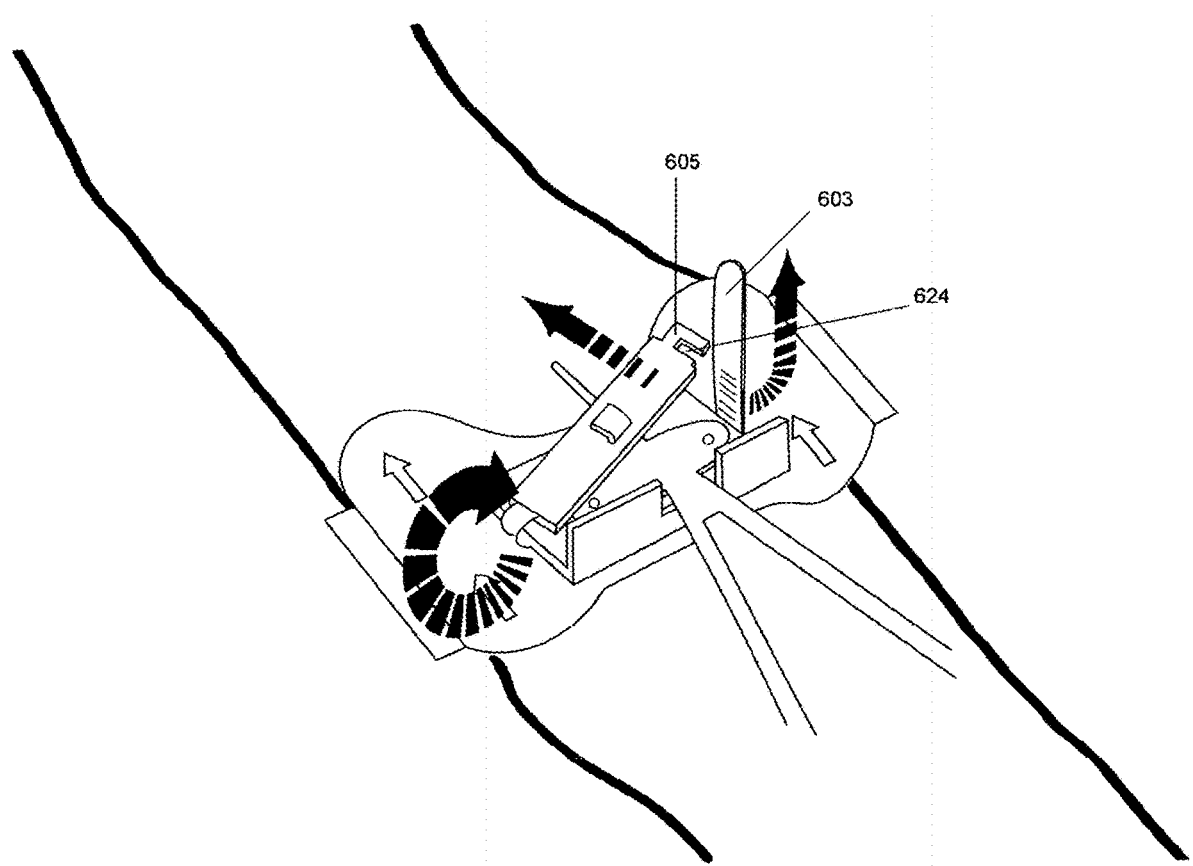
FIG. 26 is a top view of a preferred embodiment of a securement member for a central IV catheter showing transverse and longitudinal articulation of the cove and a transverse articulation of the gear ratchet strap prior to the engagement of a primary locking device with gear rack strap.
Figure 27:
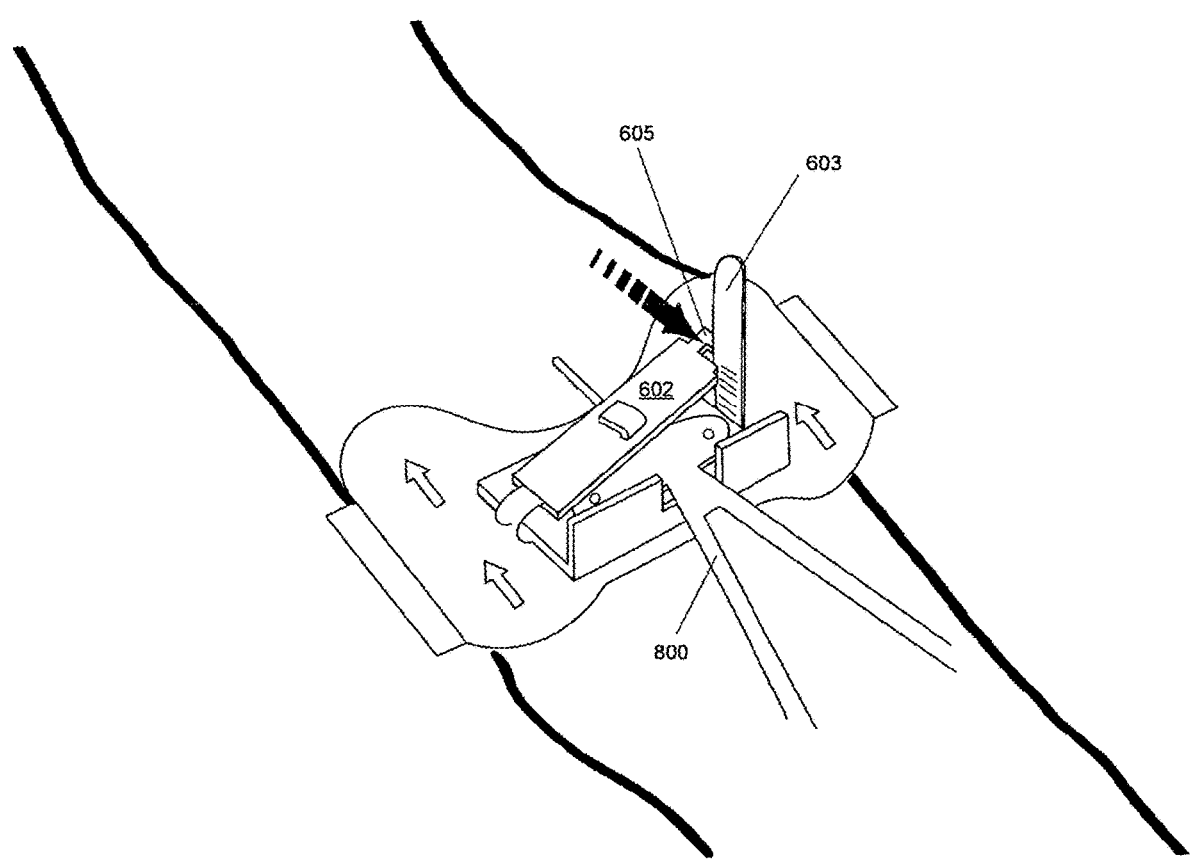
FIG. 27 is a perspective view of preferred embodiment of a securement member for a central IV catheter showing the engagement between the gear rack strap and the primary locking device.
Figure 28:
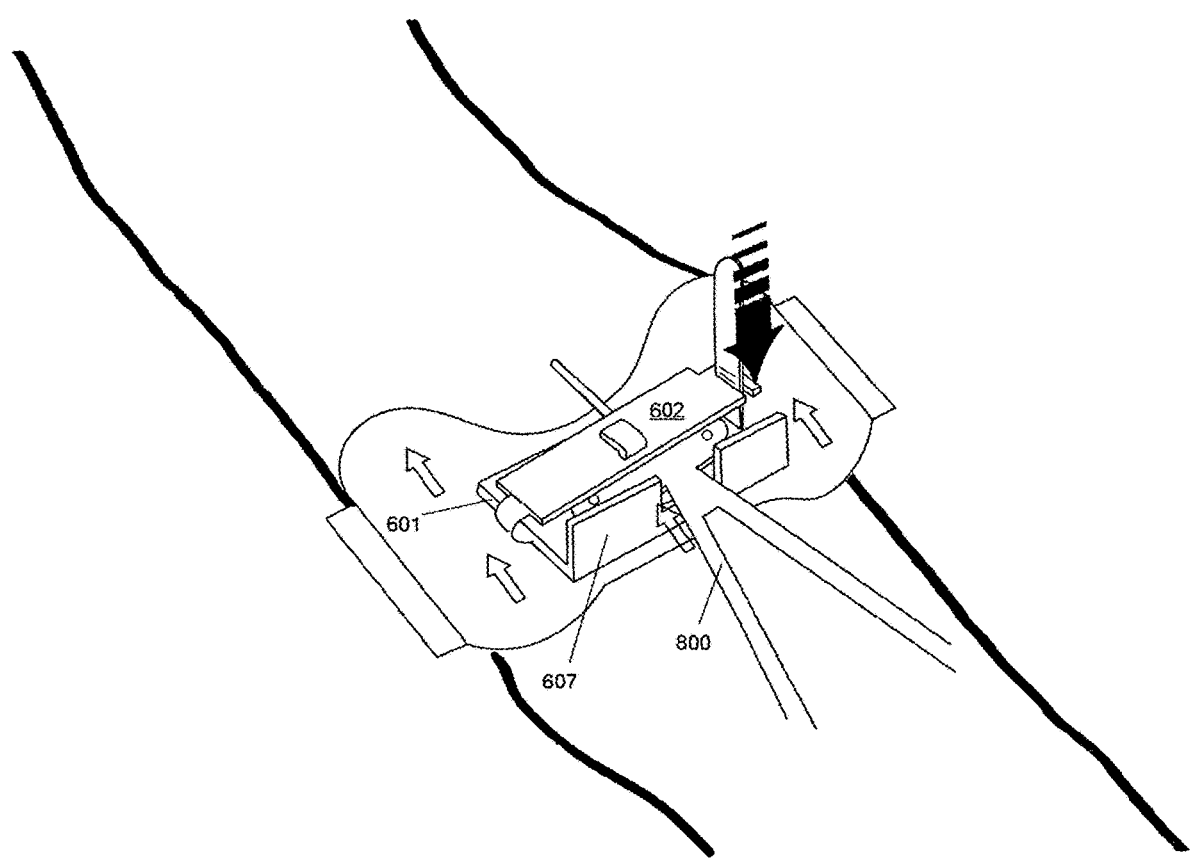
FIG. 28 is a perspective view of a preferred embodiment of a securement member for a central IV catheter showing the application of vertical force on the cover to secure the medical implement between the cover and the base.
Figure 29:
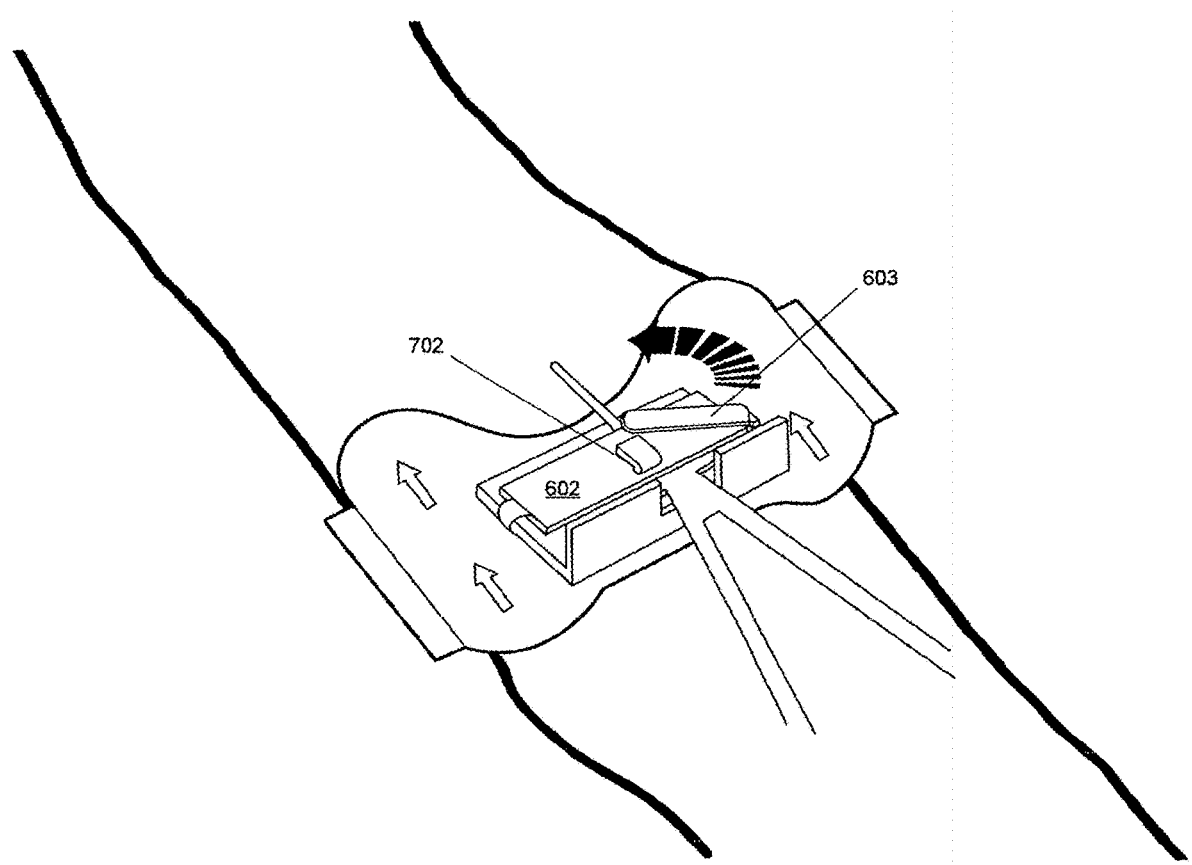
FIG. 29 is a perspective view of a preferred embodiment of a securement member for a central IV catheter showing the transverse and longitudinal movement of a gear rack strap prior to engagement with the secondary locking site.
Figure 30:
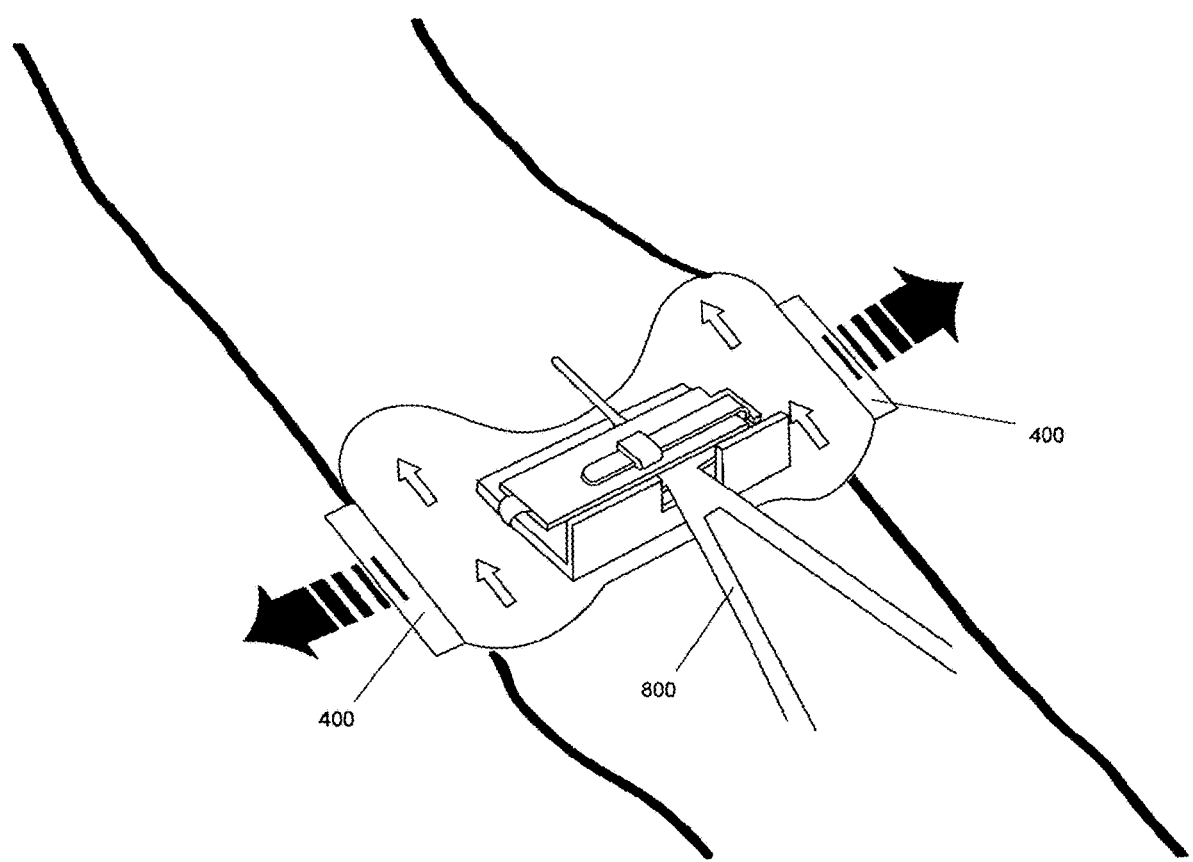
FIG. 30 is a perspective view of preferred embodiment of a securement member for a central IV catheter showing the gear rack strap being engaged with the secondary locking site and sideways removal of release paper to secure the device to the skin of the patient; and, FIG. 31 is a perspective view of the preferred embodiment of a securement member for a central IV catheter secured to a patient.
Figure 31:
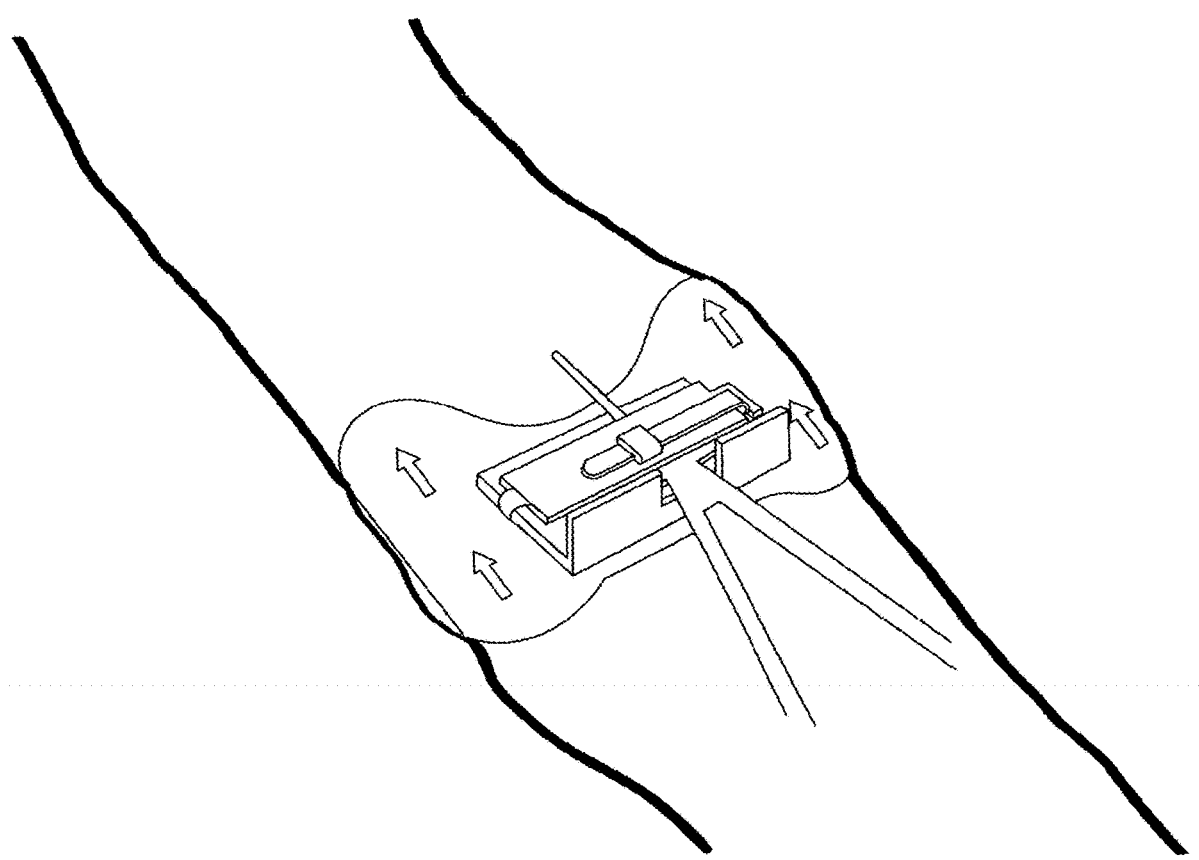

In application, the release paper 400 is removed from the top side of the device and device is placed under the wings of a catheter and attached by adhesive to the catheter. As shown in FIG. 25, a catheter 800 is aligned in the cut out position of the ridge 607 with wings 802 placed against the ridge 607. To close, a user folds the cover 602 over the catheter wings 802 and pushes slightly forward towards the insertion site. As shown in FIG. 26, the gear rack strap 603 is placed in a vertical position. With the gear rack strap 603 in a vertical position, the user aligns the side opening 624 of the locking case 605 with the gear rack 603 to engage it as shown in FIG. 27. As shown in FIG. 28, a user then pushes the cover 602 towards the base 601 and secures the catheter 800. As shown in FIG. 29, the user then moves the gear rack strap 603 over the cover 602 and pushes it into the slot 702 to lock the device closed. The user preferably places the securement device on the skin of a patient and removes the release paper 400 on site when securing the device to the patient's skin as shown in FIG. 30. FIG. 31 shows the device in closed and locked position on the patient.

The alternative embodiments in FIGS. 10-21 are designed to secure intravenous catheters, commonly referred to as peripheral and central IV catheters. These embodiments are designed for use in protecting IV catheter insertion sites as well as securing the I.V. catheters. These embodiments are capable of securing peripheral and central IV catheters at all sites where IV catheters are typically inserted.

Thus, an improved securement device for peripheral IV catheters is described above that is less bulky, simpler, more flexible and more compact, and provides for Luer interconnection to be placed on a foam cushion rather than directly on a patient's skin. This helps prevent pressure-caused trauma to the skin. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions.

Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A securement device for peripheral IV catheters, the securement device comprising:
    a base comprising an insertion site viewing window connected to a luer interconnection cushion at an articulation point and separated from the cushion by a gap;
    where the base has a top surface and a bottom surface and the bottom surface further comprises an adhesive; and,
    a cover with a luer interconnection window and a top surface and a bottom surface, where the bottom surface further comprises an adhesive and where the cover is connected to the cushion at a lateral pivot.

2. The securement device of claim 1 where the base further comprises breather holes.

3. The securement device of claim 1 where the device further comprises a first and second set of release paper attached to the bottom surface of the base, the first set of release paper covering the adhesive of the insertion site viewing window and the second set of release paper covering the adhesive of the luer interconnection cushion.

4. The securement device of claim 1 where the base and cover comprise adhesive foam padding and the insertion site viewing window comprises polyurethane film.

5. A securement device for peripheral IV catheters, the securement device comprising:
    a base comprising an insertion site viewing window connected to a luer interconnection cushion at an articulation point and separated from the cushion by a gap;
    where the base has a top surface and a bottom surface and the bottom surface further comprises an adhesive; and,
    a cover with a luer interconnection window and a top surface and a bottom surface, where the bottom surface further comprises an adhesive; and,
    where the articulation point further comprises a set of perforations such that the interconnection cushion can be separated from the insertion site viewing window.

* * * * *